United States Patent [19]

Auguello et al.

[11] Patent Number: 5,747,067
[45] Date of Patent: May 5, 1998

[54] CO-PROCESSED PRODUCTS

[75] Inventors: Michael Auguello, Marlboro, N.J.; Thomas A. Ruszkay, Hockessin, Del.; George E. Reier, Somerset, N.J.

[73] Assignee: FMC Corporation, Philadelphia, Pa.

[21] Appl. No.: 761,582

[22] Filed: Dec. 6, 1996

[51] Int. Cl.$^6$ .............................. A61K 9/20; A61K 9/26; A61K 33/10; A61K 9/14

[52] U.S. Cl. .............. 424/464; 424/465; 424/687; 424/488; 424/489

[58] Field of Search .................... 424/156, 500, 424/484, 488, 489, 464, 469, 470, 465, 687; 514/781; 106/162, 163.1

[56] References Cited

U.S. PATENT DOCUMENTS 2,599,091   6/1952   Craig.

4,744,987   5/1988   Mehra et al. .................. 424/156

FOREIGN PATENT DOCUMENTS 0193984   9/1986   European Pat. Off. .

*Primary Examiner*—Lila Feisee
*Assistant Examiner*—Susan Ungar
*Attorney, Agent, or Firm*—Robert L. Andersen; Anthony L. Cupoli

[57] ABSTRACT

Particulate pharmaceutical tablet excipient compositions comprising co-processed microcrystalline cellulose and particulate USP calcium carbonate having a particle size distribution of 7 to 22 μm wherein the range of calcium carbonate to microcrystalline cellulose is 70:30 to 90:10.

6 Claims, No Drawings

CO-PROCESSED PRODUCTS

The present invention concerns improved particulate pharmaceutical tablet excipients comprising co-processed microcrystalline cellulose (MCC) and calcium carbonate having a particle size range of 7 to 22 microns (μm).

U.S. Pat. No. 2,599,091 to Craig, discloses a method of making pigmented paper by treating cellulose fibers (wood pulp) with a strong aqueous solution of calcium chloride to hydrate and gelatinize the fibers, followed by treatment with aqueous sodium carbonate (soda ash) solution to precipitate calcium carbonate (soda ash) in, on and within the calcium chloride treated fibers (col. 8 lines 59–68; col. 1 lines 1–30). A small amount of the modified, pigmented fiber stock is then mixed with other wood pulp and the mixture used to make pigmented paper (col. 3, lines 20–48). The thrust of the '091 patent is to prepare pigmented paper stock made from cellulose fibers not cellulose in powder form.

U.S. Pat. No. 4,744,987 disclosed particulate, co-processed compositions prepared by forming a well dispersed aqueous slurry of MCC and calcium carbonate, preferably precipitated calcium carbonate (col. 3, lines 63 to 68). The patent does not exclude any source of particulate calcium carbonate from being used, however, precipitated calcium carbonate is preferred over ground limestone. This patent teaches that it is preferred to use precipitated calcium carbonate because it is purer and it has a finer particle size than ground calcium carbonate. This patent discloses $CaCO_3$ sizing which is such that all particles are less than 30 μm in size, and more preferably, less than 10 μm. Average particle size of the calcium carbonate is desirably less than 5 μm and more preferably less than 2 μm. The only example utilized precipitated calcium carbonate having an average particle size of about 1 μm. At the time of writing of this patent application (1996) commercially available precipitated calcium carbonate has a maximum particle size of about 5 μm. Using currently available precipitated calcium carbonate maximum weight ratios of MCC to $CaCO_3$ was 75:25 to 35:65 with the MCC and $CaCO_3$ being intimately associated.

In accordance with the present invention, co-processed compositions are provided which contain microcrystalline cellulose and very pure, U.S.P. particulate calcium carbonate. The particle size of the calcium carbonate is between about 7 μm and about 22 μm, preferably between about 10 and about 18 μm, more preferably between about 12 and about 18 μm, and most preferably about 15±2 μm. The usable range of calcium carbonate to microcrystalline cellulose is about 70:30 to about 90:10: however, a preferable range is about 80:20 to about 85:15 which provides the best balance of properties. USP (precipitated) calcium carbonate is lower in loose bulk density than USP calcium carbonate (ground limestone) and does not compress in the co-processed product at the 90:10 ratio.

The particulate co-processed compositions, of this invention, are prepared by forming a well-dispersed slurry of USP calcium carbonate having a particle size between about 7 and about 22 μm and microcrystalline cellulose in water and then drying the slurry, preferably by spray drying. The resultant co-processed particulate product particle size is substantially less than a 50 mesh sieve (297 microns [μm]) ASTM: E-11. The particle size distribution is generally in the range of from several μm to several hundred μm. The relative amounts of the two components are adjusted in the slurry to provide the component ratio of 70:30 to 90:10 of calcium carbonate to microcrystalline cellulose.

USP calcium carbonate (ground limestone) is the calcium carbonate of choice at the present time because it provides a broader range of useful MCC to calcium carbonate ratios than does precipitated calcium carbonate. Precipitated calcium carbonate having the desired particle size distribution, between about 7 and about 22 μm, if it became available, such material would be a calcium carbonate of choice. Another advantage of the preferred co-processed excipients containing 70% or more ground limestone is the increased loose bulk density of the excipient. This increased density permits smaller tablets to made, and the reduced tablet size is, in part, responsible for the elegant appearance of tablets prepared using these excipients. Additionally, these excipients provide a more uniform surface, providing a smooth, elegant appearance to the tablets made therefrom.

The friability of caplets prepared from the co-processed calcium carbonate/microcrystalline cellulose excipients of this invention is quite low, ranging from 0 to less than 0.6%, well within USP standards.

The co-processed compositions of the invention contain higher levels of calcium carbonate and proportionally lower levels of MCC than can be obtained using the teachings of U.S. Pat. No. 4,744,987. This higher level of calcium carbonate in the excipient reduces excipient costs. Tablet weight variability improves as the percentage of calcium carbonate increases in the excipient. This trend is the inverse of the loose bulk density which increases with increasing calcium carbonate content. One contributing factor to the reduced variability in tablet weight is the improved flow rates. These improved flow rates are responsible for more rapid, even flow into tableting dies, filling them completely and uniformly, when producing vitamin tablets.

Although not necessarily responsible for the improved tablet weight variability, the water content of the spray dried co-processed excipient decreases with increasing calcium carbonate content. This decrease in water content is not surprising in that microcrystalline cellulose doubtless binds more water than does calcium carbonate. Disintegration times of tablets of this invention are clearly very short, particularly with the preferred purified, ground limestone. These times are well within the USP standards for disintegration to make less soluble actives readily available for dissolution.

The co-processed calcium carbonate/microcrystalline tablet excipients of this invention are primarily intended for use in vitamin caplets, although they may find utility in many types of compressed tablets. One advantage inherent in these excipients is that in vitamin tablets they provide increased calcium content. This is important in vitamins which are intended to counteract osteoporosis in aging adults who are susceptible to the ravages of this disease.

Although not evident from the examples appended hereto, the excipients of this invention are useful for improved carrying of actives which have a low density, 0.25–0.30 g/mL. The increased density of the excipient is responsible for this effect.

The following examples further illustrate the invention and to demonstrate the advantages of the co-processed 70:30 to 90:10 calcium carbonate:microcrystalline cellulose excipients. In all cases these were made using a hydrolyzed cellulose pulp which was not attrited. Example 1 details the process by which all co-processed excipient samples were made.

Unless indicated otherwise the samples were prepared using purified USP calcium carbonate (ground limestone) having a particle size of 15±2 μm.

Example 2 describes a complete vitamin formulation. In this example the exact formulation, which is a commercially available one, is somewhat less detailed to avoid fully

3 describing the vitamin content. Examples 3 and 4 show the relative properties of various ratios prepared from USP calcium carbonate (ground limestone) and precipitated calcium carbonate, respectively; the 50:50 co-processed material is included for comparative purposes.

EXAMPLE 1

Preparation of an 80:20 co-processed blend of ground limestone:microcrystalline cellulose In a 757 liter (200 gal) tank is placed 227.1 liters (60 gal) of deionized water. To this water is added with stirring 72.58 kilograms (160 lbs) of purified USP calcium carbonate (ground limestone) having a particle size of 15±2 µm. Subsequently, 52.16 kilograms (115 lbs, 35% solids) of softwood pulp which has been hydrolyzed with hydrochloric acid, but not attrited, is added to the slurry and is completely dispersed with a low-shear mixer. This slurry containing 26 wt % solids is then milled in a commercial colloid mill and transferred into a 1514 liter (400 gal) tank from which it is pumped to a 2.44 meter (8 foot) Bowen spray dryer. The disk is operated at 14,062 rpm. The inlet temperature of the dryer is 204.4° C. (400° F.) and the outlet temperature is 82.2° C. (180° F.). The resulting co-processed powder contains an 80:20 ratio of calcium carbonate to microcrystalline cellulose and 1 wt % water. The particle size distribution of the co-processed product is from about 1 to about 300 µm. The loose bulk density of this material is 0.667 grams/mL.

EXAMPLE 2

A multi-vitamin/mineral formulation containing the 80:20 co-processed blend of ground limestone:microcrystalline cellulose In a large twin shell blender are mixed 111.304 grams of triturated minerals, 1000.624 grams of a blend of common vitamins, 1594.0 grams of a vitamin/mineral granulation, 19.84 grams of colloidal silica, 160 grams of croscarmellose sodium (Ac-Di-Sol®, sold by FMC Corporation, Philadelphia, Pa.), 620 grams of tricalcium phosphate, 1752 grams of the 80:20 co-processed calcium carbonate:microcrystalline cellulose (prepared in Example 1), 14.0 grams of stearic acid, and 20 grams of magnesium stearate. Blending is continued until the composition is uniform. The particle size distribution of the co-processed product is from about 1 to about 300 µm. The loose bulk density of the vitamin/mineral containing co-processed material is 0.734 grams/mL. Caplets are prepared using a Stokes B-2 rotary tablet press fitted with caplet-shaped tooling measuring 18.8 mm by 8.9 mm (0.740 inch by 0.350 inch). These caplets are embossed with "FMC" and a bisect. A lower compression force 2269 Kilograms yields caplets having an average hardness of 11.21 Kiloponds. The average weight of ten caplets is 12.91 grams and their thickness is 7.01 mm (0.2761 inch). The disintegration time is determined using 6 tablets by the USP 23, pages 1790–1791, method with disks, in 900 mL of purified water at 37° C. The disintegration time is 135 seconds. The friability after four minutes in a Roche Friability Tester is found to −0.584%. In addition to the above properties, these tablets have an excellent appearance.

Caplets are aged at room temperature, 35° C., and 45° C. for one, two, and three months. At the end of these periods of aging, caplets are tested for weight, thickness, hardness and disintegration times by the methods described above. The results of these aging studies are presented in Table 1.

Aging, both room temperature and accelerated aging, does not produce any significant changes in the properties of these multi-vitamin caplets.

4

EXAMPLE 3

Comparison of properties of neat 50:50, 80:20, 85:15, and 90:10 ground limestone:microcrystalline cellulose Co-processed compositions composed of 50:50, 80:20, 85:15, and 90:10 ratios of USP calcium carbonate (ground limestone) to microcrystalline cellulose are prepared in the manner of Example 1. In addition, the water content, loose bulk density and the flow rate are measured for each sample. The flow rate determination is made using a funnel flow tester which measures the time that is required for 590 grams of material to flow through the standard opening. Each sample is then compressed neat, i.e., without addition of any active ingredients or lubricants, into caplets using a Stokes B-2 rotary tablet press fitted with caplet-shaped tooling measuring 18.8 mm by 8.9 mm (0.740 inch by 0.350 inch). These caplets are embossed with "FMC" and a bisect. The upper and lower compression forces and the ejection force are measured for each composition. The weights, thicknesses, friability, and hardness of ten caplets are measured and averaged. Also, the disintegration times of six caplets are measured by the method described in Example 2 and the average results reported. The results of these measurements are recorded in Table 2.

EXAMPLE 4

Comparison of properties of neat 50:50, 80:20, 85:15, and 90:10 precipitated calcium carbonate:microcrystalline cellulose Co-processed compositions composed of 50:50, 80:20, 85:15, and 90:10 ratios of precipitated calcium carbonate (particle size 5 µm) to microcrystalline cellulose are prepared in the manner of Example 1. In addition, the water content, loose bulk density and the flow rate are measured for each sample. The flow rate determination is made by the method described in Example 3. Each neat sample is then compressed into caplets using a Stokes B-2 rotary tablet press fitted with caplet-shaped tooling measuring 18.8 mm by 8.9 mm (0.740 inch by 0.350 inch) These caplets are embossed with "FMC" and a bisect. The upper and lower compression forces and the ejection force are measured for each composition. The weights, thicknesses, and hardness of ten caplets are measured and averaged. Also, the disintegration times of six caplets are measured by the method described in Example 2 and the average results reported. The results of these measurements are recorded in Table 3.

TABLE 1

| Aging time and conditions | Tablet weight (grams) | Thickness (inch) | Hardness (Kilopounds) | Disintegration (seconds) |
| --- | --- | --- | --- | --- |
| One month | | | | |
| Room Temp. | 12.909 | 0.2756 | 10.9 | 136 |
| 35° C. | 12.952 | 0.2764 | 10.3 | 169 |
| 45° C. | 12.938 | 0.2778 | 11.5 | 152 |
| Two months | | | | |
| Room Temp. | 12.916 | 0.2769 | 10.8 | 158 |
| 35° C. | — | 0.2778 | 10.2 | 172 |
| 45° C. | 12.960 | 0.2775 | 11.1 | 134 |
| Three months | | | | |
| Room Temp. | 12.918 | 0.2755 | 11.3 | 122 |
| 35° C. | 12.900 | 0.2765 | 11.1 | 120 |

TABLE 1-continued

| Aging time and conditions | Tablet weight (grams) | Thickness (inch) | Hardness (Kilopounds) | Disintegration (seconds) |
|---|---|---|---|---|
| 45° C. | 12.876 | 0.2783 | 11.5 | 130 |

TABLE 2

| CaCO$_3$:MCC | 50:50 | 80:20 | 85:15 | 90:10 |
|---|---|---|---|---|
| Particle Sizes | | | | |
| (microns) | (percent) | | | |
| >297 | 0.55 | 0.17 | 0.13 | 0.36 |
| 177–297 | 1.35 | 0.26 | 0.13 | 0.13 |
| 149–177 | 3.85 | 1.00 | 0.63 | 0.44 |
| 74–149 | 33.51 | 25.04 | 21.00 | 17.42 |
| 53–74 | 17.90 | 23.46 | 15.77 | 13.15 |
| <53 | 42.84 | 50.07 | 62.34 | 68.50 |
| Water (%) | 1.25 | 0.25 | 0.25 | 0.25 |
| Loose bulk density (g/mL) | 0.513 | 0.656 | 0.692 | 0.701 |
| Flow rate (sec) | 33.0 | 24.3 | 21.2 | 30.7 |
| Tablet Properties | | | | |
| Weight (grams) | 9.865 | 9.683 | 10.182 | 9.880 |
| Weight variability (%) | 2.15 | 1.50 | 1.40 | 0.80 |
| Thickness (mm) | 6.82 | 5.72 | 5.52 | 5.17 |
| Hardness (Kp) | 13.0 | 13.3 | 15.3 | 9.4 |
| Friability (% loss) | 0.0203 | 0.0204 | 0.0444 | 0.202 |
| Disintegration time (sec) | 17.13 | 14.72 | 16.10 | 25.05 |
| Compression Forces (Kilograms) | | | | |
| Upper | 951.88 | 1324.63 | 1705.75 | 1920.72 |
| Lower | 876.25 | 1223.13 | 1567.88 | 1741.29 |
| Ejection | 29.19 | 42.03 | 50.76 | 45.40 |

TABLE 3

| CaCO$_3$:MCC | 50:50 | 80:20 | 85:15 | 90:10 |
|---|---|---|---|---|
| Particle Sizes | | | | |
| (microns) | (percent) | | | |
| >297 | 1.08 | 0.67 | 0.69 | 2.47 |
| 177–297 | 0.61 | 0.94 | 0.68 | 1.02 |
| 149–177 | 3.48 | 4.93 | 1.74 | 0.92 |
| 74–149 | 24.87 | 28.61 | 17.78 | 14.89 |
| 53–74 | 8.60 | 5.57 | 4.87 | 7.64 |
| <53 | 61.36 | 59.28 | 74.24 | 73.06 |
| Water (%) | 1.50 | 1.00 | 0.50 | 0.25 |
| Loose bulk density (g/mL) | 0.423 | 0.411 | 0.383 | 0.372 |
| Flow rate (sec) | 80.9 | 63.6 | 69.9 | none |
| Tablet Properties | | | | |
| Weight (grams) | 10.113 | 9.745 | 10.20 | * |
| Thickness (mm) | 6.69 | 6.21 | 6.41 | |
| Hardness (Kp) | 23.28 | 12.73 | 10.06 | |
| Friability (% loss) | 0.119 | 0.147 | 0 | |
| Disintegration time (sec) | 75 | 30.4 | 36.7 | |
| Compression Forces (Kilograms) | | | | |
| Upper | 1404.7 | 1325.8 | 1272.4 | |
| Lower | 1476.2 | 1280.3 | 1319.3 | |
| Ejection | 22.17 | 58.90 | 60.86 | |

(a) The 90:10 composition of precipitated calcium carbonate:microcrystalline cellulose cannot be compressed into caplets, hence no values are reported.

What is claimed is:

1. Particulate pharmaceutical tablet excipient compositions comprising co-processed microcrystalline cellulose and particulate USP calcium carbonate, in which the calcium carbonate has an average particle size in the range of 7 to 22 μm and the weight ratio of calcium carbonate to microcrystalline cellulose is in the range of 70:30 to 90:10.

2. The composition of claim 1 wherein the calcium carbonate has a particle size of 10 to 18 μm.

3. The composition of claim 2 wherein the calcium carbonate has a particle size of 15±2 μm.

4. The composition of claim 1 wherein the range of calcium carbonate to microcrystalline cellulose is 80:20 to 85:15.

5. The composition of claim 4 wherein the calcium carbonate has a particle size of 12 to 18 μm.

6. The composition of claim 5 wherein the calcium carbonate has a particle size of 15±2 μm.

* * * * *

UNITED STATES PATENT AND TRADEMARK OFFICE
CERTIFICATE OF CORRECTION

PATENT NO. : 5,747,067
DATED : May 5, 1998
INVENTOR(S) : Augello et al.

It is certified that error appears in the above-identified patent and that said Letters Patent is hereby corrected as shown below:

Title page, under item [19] and item [75] delete "Auguello" and insert --"Augello"--.

Signed and Sealed this

First Day of September, 1998

Attest:

BRUCE LEHMAN

*Attesting Officer*              *Commissioner of Patents and Trademarks*